United States Patent
Das et al.

(10) Patent No.: US 6,653,497 B1
(45) Date of Patent: Nov. 25, 2003

(54) DICYANATOCHALCONES AND METHOD FOR THE PRODUCTION THEREOF

(75) Inventors: Sajal Das, Bedminster, NJ (US); Ulrich Daum, Hofstetten (CH); Marion Fengler-Veith, Zurich (CH); Pascal Willa, Getwing (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/048,472

(22) PCT Filed: Aug. 7, 2000

(86) PCT No.: PCT/EP00/07629

§ 371 (c)(1),
(2), (4) Date: May 29, 2002

(87) PCT Pub. No.: WO01/10824

PCT Pub. Date: Feb. 15, 2001

Related U.S. Application Data
(60) Provisional application No. 60/152,250, filed on Sep. 3, 1999.

(30) Foreign Application Priority Data

Aug. 10, 1999 (EP) .............................. 99115759

(51) Int. Cl.⁷ .......................................... C07C 255/00
(52) U.S. Cl. ....................................... 558/343; 558/345
(58) Field of Search ................................ 558/343, 345

(56) References Cited

U.S. PATENT DOCUMENTS

| | | | |
|---|---|---|---|
| 4,713,442 A | * 12/1987 | Woo et al. ................... | 528/422 |
| 4,851,279 A | * 7/1989 | Das et al. ................... | 428/224 |
| 4,970,276 A | * 11/1990 | Das et al. ................... | 525/504 |
| 4,988,780 A | 1/1991 | Das et al. ................... | 525/504 |
| 5,043,214 A | 8/1991 | Das et al. ................... | 428/329 |

FOREIGN PATENT DOCUMENTS

WO 9001514 2/1990

OTHER PUBLICATIONS

Patent Abstracts of Japan, vol. 1999, No. 4, (Apr. 30, 1999), Publication No. 11021503.
Patent Abstracts of Japan, vol. 1999, No. 4, (Apr. 30, 1999), Publication No. 11021504.

* cited by examiner

*Primary Examiner*—Sabiha Qazi
(74) *Attorney, Agent, or Firm*—Fisher, Christen & Sabol

(57) ABSTRACT

Dicyanatochalcones of general formula:

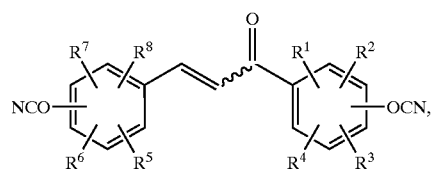

I wherein $R^1$ to $R^8$, independent of one another, represent hydrogen, $C_{1-4}$-alkyl, $C_{1-4}$-alkoxy or halogen. The compounds can be produced from corresponding dicyanatochalcones by reacting them with chlorine cyanide or bromine cyanide and with a tertiary amine. The compounds are suited for producing polytriazine resins exhibiting good mechanical properties, a low dielectric constant and a good behavior in fire.

7 Claims, No Drawings

DICYANATOCHALCONES AND METHOD FOR THE PRODUCTION THEREOF

This is a 371 of PCT/EP00/07629, filed on Aug. 7, 2000, that has benefit of Provisional Application No. 60/152,250, filed on Sep. 3, 1999, and has benefit of European Patent Application No. 99115759.5, filed on Aug. 10, 1999.

The invention relates to dicyanatochalcones of the general formula

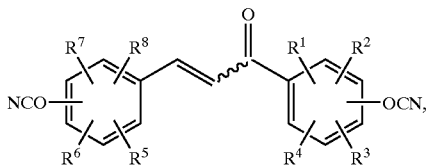

I in which $R^1$ to $R^8$ independently of one another are hydrogen, $C_{1-4}$-alkyl, $C_{1-4}$-alkoxy or halogen.

Here and below, $C_{1-4}$-alkyl is to be understood as meaning all linear or branched primary, secondary and tertiary alkyl groups having 1 to 4 carbon atoms, i.e. methyl, ethyl, propyl, isopropyl, butyl, isobutyl, sec-butyl and tert-butyl.

Correspondingly, $C_{1-4}$-alkoxy is to be understood as meaning the groups composed of $C_{1-4}$-alkyl and oxygen.

Halogen is to be understood as meaning fluorine, chlorine, bromine and iodine, in particular chlorine and bromine.

Difunctional aromatic cyanates, such as, for example, 2,2-bis-(4-cyanatophenyl)propane, which is derived from bisphenol A, are starting materials for polytriazine resins which, due to their high heat resistance and favourable mechanical and electrical properties, are used more and more frequently. In spite of these advantages, their properties are not yet satisfactory in all respects. Thus, for example, flexibility, impact strength, elongation at break and tear strength are insufficient for certain applications, and the exothermic reaction during curing may furthermore lead to problems.

Accordingly, it was the object of the present invention to provide novel aromatic cyanates which liberate little heat during cyclotrimerization to give polytriazines and yield polytriazines having improved mechanical properties.

This object is achieved according to the invention by the dicyanatochalcones of the invention.

It has been found that dicyanatochalcones of the general formula

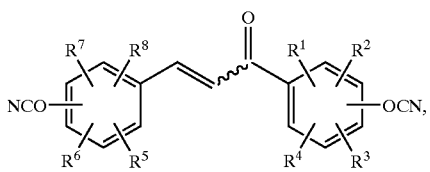

I in which $R^1$ to $R^8$ independently of one another are hydrogen, $C_{1-4}$-alkyl, $C_{1-4}$-alkoxy or halogen, give off only little heat during cyclotrimerization to give polytriazines. Furthermore, they yield polytriazine resins having high flexibility, impact strength, tear strength and elongation at break and a low permittivity. Moreover, in the event of fire, they give off only small amounts of low-toxicity flue gas. Furthermore, the peak heat release during combustion of the cured resins and/or components is extremely low compared to the cyanate esters or other resin systems which have been available to date.

Particular preference is given to 1,3-bis-(4-cyanatophenyl)-2-propen-1-one of the formula

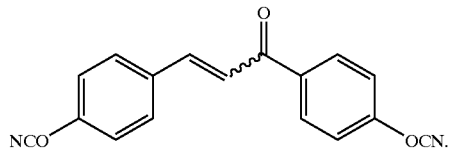

The dicyanatochalcones according to the invention can be prepared by reacting a dihydroxychalcone of the general formula

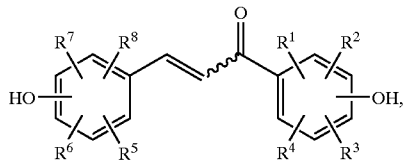

II in which $R^1$ to $R^8$ are as defined above with cyanogen chloride or cyanogen bromide and a tertiary amine.

The dihydroxychalcones (II) are known compounds, or they can be obtained from the corresponding substituted benzaldehydes and acetophenones, analogously to known processes.

The reaction of the dihydroxychalcone (II) is preferably carried out using cyanogen chloride.

A particularly preferred tertiary amine is triethylamine.

The examples below illustrate the preparation of the compounds according to the invention, without imposing any limitations.

EXAMPLE 1

1,3-Bis-(4-cyanatophenyl)-2-propen-1-one 10 g (41.5 mmol) of 1,3-bis-(4-hydroxyphenyl)-2-propen-1-one were initially charged in a double-walled reactor (250 ml) fitted with stirrer, thermometer, gas inlet tube and a metering pump for liquors. After addition of 140 ml of anhydrous acetone, the solution was cooled to −10° C. Over a period of 10 minutes, 5.63 g (91.5 mmol) of cyanogen chloride were then introduced initially, followed by the metered addition, with vigorous stirring, of 8.55 g (84.5 mmol) of triethylamine at a flow rate of approximately 0.4 ml/min, during which the temperature of the reaction mixture was kept below −10° C. at all times. The reaction mixture was then warmed to 20° C., stirred at this temperature for 30 minutes and once more cooled to 0° C. The triethylammonium chloride that had formed was filtered off and washed with cold acetone (2×50 ml). The filtrate was concentrated to 70 g using a rotary evaporator (20 mbar, bath temperature 40° C.), then, at 20° C., admixed with the same amount of water and finally cooled to 5° C. The crystalline product was filtered off and dried in a vacuum drying cabinet at 20 mbar/50° C. for 16 hours. More product was obtained by evaporating the mother liquor and recrystallizing the residue from aqueous acetone.

M.p.: 172–174° C.

$^1$H NMR ($d_6$-DMSO): δ=7.54–7.65 (AA'XX', 4H); 7.77–8.00 (AB, 2H); 8.09–8.36 (AA'XX', 4H)

$^{13}$C NMR ($d_6$-DMSO): δ=107.9; 108.2; 115.9 (2C); 116.1 (2C); 122.9; 131.3 (2C); 131.5 (2C); 133.6; 136.0; 142.5; 153.5; 155.2.

IR (KBr): ν=3063 (m, CH); 2268, 2235 (vs, OCN); 1717 (w); 1667 (vs); 1615 (m); 1598 (s); 1591 (s); 1500 (s); 1421 (m); 1344 (m); 1328 (m); 1312 (w); 1210 (vs); 1196 (vs); 1167 (s) ; 1109 (w) ; 1087 (w) ; 1032 (m); 1010 (m); 989 (m); 821 (s); 801 (m); 784 (w); 501 (m); 493 (w) cm$^{-1}$.

EXAMPLE 2

1,3-Bis-(4-cyanatophenyl)-2-propen-1-one 10 g (41.5 mmol) of 1,3-bis-(4-hydroxyphenyl)-2-propen-1-one were initially charged in a double-walled reactor (250 ml) fitted with stirrer, thermometer, gas inlet tube and a metering pump for liquors. After addition of 110 ml of anhydrous acetone, the solution was cooled to −10° C. Over a period of 10 minutes, 5.63 g (91.5 mmol) of cyanogen chloride were then introduced initially, followed by the metered addition, with vigorous stirring, of 8.55 g (84.5 mmol) of triethylamine at a flow rate of approximately 0.4 ml/min, during which the temperature of the reaction mixture was kept below −10° C. at all times. The reaction mixture was then warmed to 20° C. and stirred at this temperature for 30 minutes. Over a period of 10 minutes, the reaction mixture was subsequently added with vigorous stirring to 200 ml of water which had been cooled to 5° C. beforehand. The suspension was then stirred for 30 minutes, slowly warmed to 15° C. and filtered. The filter cake was washed with water (2×30 ml) and dried in a vacuum drying cabinet at 20 mbar/50° C. for 20 hours. In this manner, 11.03 g (92%) of cyanate having a melting point of 171–173° C. were isolated.

What is claimed is:

1. A dicyanatochalcone of formula:

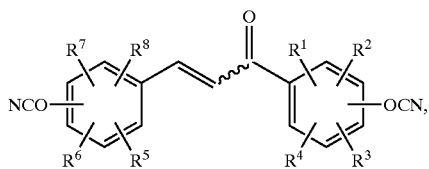

in which $R^1$ to $R^8$, independently of one another, are hydrogen, $C_{1-4}$-alkyl, $C_{1-4}$-alkoxy or halogen.

2. 1,3-Bis-(4-cyanatophenyl)-2-propen-1-one of formula:

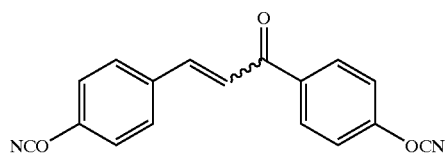

3. A process for preparing a dicyanatochalcone of formula:

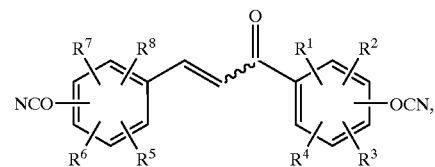

in which $R^1$ to $R^8$, independently of one another, are hydrogen, $C_{1-4}$-alkyl, $C_{1-4}$-alkoxy or halogen, comprising reacting a dihydroxychalcone of formula:

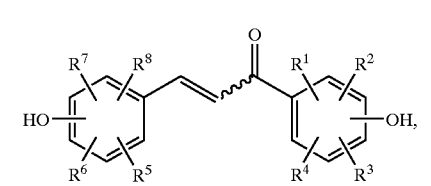

in which $R^1$ to $R^8$ are as defined above, with cyanogen chloride or cyanogen bromide and a tertiary amine.

4. The process according to claim 3, wherein the reaction is carried out using cyanogen chloride.

5. The process according to claim 4, wherein the tertiary amine is triethylamine.

6. The process according to claim 3, wherein the tertiary amine is triethylamine.

7. The process according to claim 6 wherein $R^1$ to $R^8$, independently of one another are methyl, ethyl, propyl, isopropyl, butyl, isobutyl, sec-butyl or tert-butyl.

* * * * *